(12) United States Patent
Jones

(10) Patent No.: US 6,253,807 B1
(45) Date of Patent: *Jul. 3, 2001

(54) APPARATUS AND PROCESS FOR LIQUID SAMPLE ALIQUOTTING

(75) Inventor: Trevor Jones, Hamiltion (CA)

(73) Assignee: CRS Robotics Corporation, Burlington (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/232,598

(22) Filed: Jan. 19, 1999

(30) Foreign Application Priority Data

Jan. 16, 1998 (GB) ................................................. 9800988

(51) Int. Cl.[7] ........................................................ G01N 1/00
(52) U.S. Cl. ............................ 141/321; 141/1; 141/319; 141/130; 141/322; 141/352; 141/357; 73/863.86; 422/63; 422/103
(58) Field of Search .................................... 141/319–322, 141/130, 1, 351–354, 357; 422/63–65, 67, 100, 102, 103; 73/863.87, 863.83, 863.86

(56) References Cited

U.S. PATENT DOCUMENTS

| 3,782,197 | 1/1974 | Grams . | |
|---|---|---|---|
| 3,985,508 | 10/1976 | Williams . | |
| 4,058,367 | 11/1977 | Gilford . | |
| 4,692,308 | 9/1987 | Riley et al. | 422/65 |
| 4,695,430 | 9/1987 | Coville et al. | 422/65 |
| 5,411,065 | 5/1995 | Meador et al. | 141/1 |
| 5,549,141 | 8/1996 | Meador et al. | 141/1 |
| 5,555,920 | * 9/1996 | Godolphin et al. | 141/320 |
| 5,702,019 | * 12/1997 | Grimard | 141/319 |
| 5,975,373 | * 11/1999 | Forsberg | 141/351 |

* cited by examiner

Primary Examiner—J. Casimer Jacyna
(74) Attorney, Agent, or Firm—Simpson, Simpson & Snyder, L.L.P.

(57) ABSTRACT

A fully automatic apparatus and process for aliquotting liquid samples from a sample container is provided which includes the steps of creating an opening in the sample container, transferring an aliquot of the sample liquid into an aliquot tube, sealing the container and conveying the aliquot tube to a location for conducting the desired tests on the sample aliquot.

1 Claim, 5 Drawing Sheets

APPARATUS AND PROCESS FOR LIQUID SAMPLE ALIQUOTTING

BACKGROUND OF THE INVENTION

1. Field of the Invention

The present invention relates generally to devices for handling containers designed for liquid sample collection and for presenting such containers to clinical analyzers.

2. Description of the Prior Art

The sampling of fluids for diagnostic or evidentiary purposes is very common. Such fluids, which include urine, blood, water, milk etc., are collected in a specimen container and transported to a laboratory where they are analyzed to determine the presence of infections or contaminants such as drugs, alcohol etc. Under such circumstances, the collected sample must be maintained uncontaminated until the various testing procedures have been concluded. Containers for this purpose are common and usually comprise a plastic container having a secure lid.

Upon arrival at the testing laboratory, portions of the sample are manually, semi-automatically or automatically removed from the sample collection container into a secondary container, usually a disposable plastic test tube. In the manual case, the sample is "aliquotted" by pouring the liquid from the collection container. In the semi-automatic case, the sample container is opened and a portion of the sample is removed by lowering a pipette tip into the liquid and extracting the desired volume. In the automatic case, the lid is either removed or punctured by the apparatus and a pipette tip is lowered into the sample for extracting the desired volume.

Since the collected sample may pose a biohazard risk, great care must be taken to ensure that the liquid sample is not spilled during the handling of the container or the extraction of the sample aliquot. For this reason, a fully automatic system for handling the sample container is preferred.

Another problem associated with the known methods lies in the aliquot extraction step using pipettes. For example, the pipettes must be disposable for high throughput and reduced contamination risk. This leads to high levels of waste and a run-time cost for the system. Further, pipette tips are very difficult to change while a fully automated system is running. In a manual or semi-automatic system, there is direct contact with the liquid and, therefore, a contamination risk.

Other disadvantages with known fully automated systems lies in designing the required apparatus for removing the caps of the sample containers. Further, the tamper resistant seals, which are used to ensure that contamination of a sample has not occurred, are difficult to remove in automated systems.

One proposed automated system and apparatus for handling sample containers is taught in U.S. Pat. No. 5,549,141. This patent teaches an apparatus designed for a particular sample container which removes the need for manual handling.

A liquid sample container which provides safe use is taught in U.S. application Ser. No. 08/879,301 (which is incorporated herein by reference). The container described in U.S. application Ser. No. 08/879,301 includes a cap which is specifically designed for dispensing an aliquot of liquid and which is also designed for a fully automated system. However, no apparatus in known which is capable of utilizing such a container.

The present invention seeks to provide a process and apparatus for removing an aliquot from the above mentioned container and to convey such aliquot to the required clinical analyzers.

SUMMARY OF THE INVENTION

In one embodiment, the present invention provides a process for removing an aliquot of a liquid sample from a sample container having a lid with a flexible member or diaphragm and a sealed opening, the process comprising:

exposing the opening in the lid of the container;

positioning an inverted aliquot tube, having an opening, above the container wherein the aliquot tube opening faces and contacts the lid opening;

simultaneously inverting both the container and the aliquot tube so that the aliquot tube is righted;

moving the aliquot tube and/or container against each other so that the flexible member of the lid is depressed so as to eject a volume of the liquid sample into the aliquot tube;

separating the container and aliquot tube;

righting the container;

heat sealing the opening in the container lid to prevent further liquid from escaping; and conveying the aliquot tube to a location for performing any desired tests on the liquid sample in the aliquot tube.

In another embodiment, the invention provides an apparatus for performing the various steps of the process. Such an apparatus comprises an apparatus for extracting a liquid sample from a sample container into an aliquot tube, the container having a lid including a flexible flange for covering an opening of the container, the lid further including a sealed opening, the apparatus comprising:

a) a means for grasping the container;

b) a means for unsealing the lid;

c) a means for positioning the aliquot tube over the container and for contacting an opening in the aliquot tube with the lid of the container whereby the lid opening opens into the aliquot tube opening;

d) a means for rotating the container and the aliquot tube while in contact with each other in order to right the aliquot tube;

e) a means for biasing the aliquot tube and/or the container against each other whereby the flexible flange of the lid is forced to bend and, thereby, expel a volume of the liquid into the aliquot tube;

f) a means for separating the container and the aliquot tube;

g) a means for sealing the container lid opening; and, h) a means for conveying the aliquot tube to a location for conducting any required tests on the extracted sample.

BRIEF DESCRIPTION OF THE DRAWINGS

These and other features of the preferred embodiments of the invention will become more apparent in the following detailed description in which reference is made to the appended drawings wherein.

DESCRIPTION OF THE PREFERRED EMBODIMENTS

Figure 1:
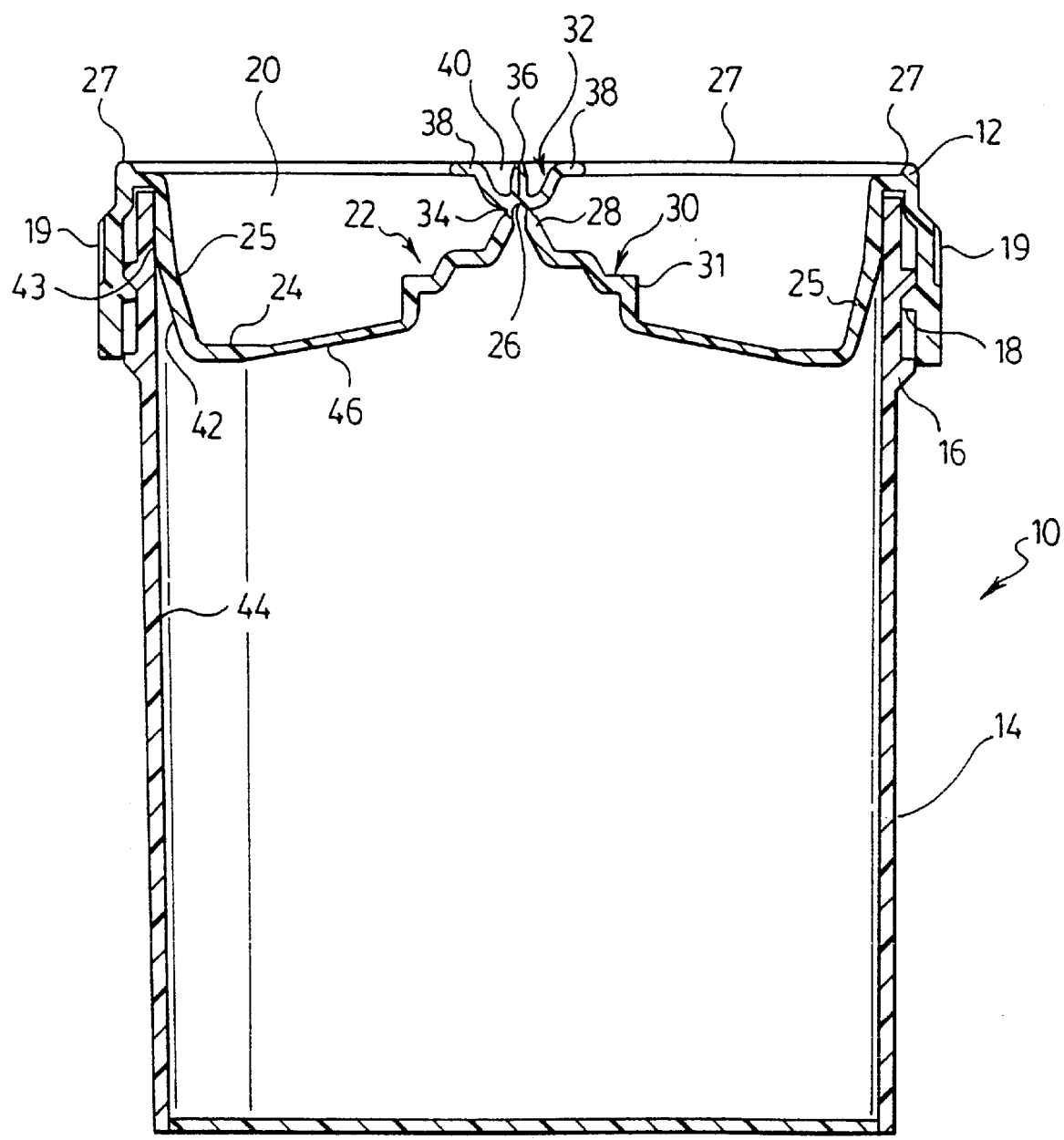
FIG. 1 is a cross sectional view through the central longitudinal axis of a sample container for use by the invention.

In FIG. 1, the container of U.S. application Ser. No. 08/879,301 is illustrated generally at 10. The container includes a lid 12 and a receptacle 14 for containing the liquid sample. The receptacle 14 is of a standard design and includes a threaded upper portion 16 which engages a corresponding threaded portion 18 of the lid 12, thereby allowing the lid to be secured to the receptacle. The lid is formed of a flexible thermoplastic material and the receptacle is of a generally cylindrical structure also formed of a thermoplastic material.

As shown in FIG. 1, the lid 12 includes a well 20 and a spout portion 22 located in the center of the lid. The well 20 of the lid 12 is bounded by a bottom surface 24 and a sidewall 25. Bottom surface 24 generally slopes upward from its junction with the sidewall 25, at the outer circumference, to the center spout portion 22. The spout portion 22 comprises a funnel 28 having an opening, or orifice, 26. The spout portion further comprises an uneven bearing surface 30 the purpose of which is described below. Bearing surface 30, in a preferred embodiment, has a plurality of ribs 31 that radiate in a direction towards the outer circumference of the lid.

The opening 26 is sealed by a closure 32, which is integrally formed with the lid 12 and is connected to the funnel 28 by means of a junction 34. The junction 34 is made of the same thermoplastic material as the funnel 28 and the closure 32 but is of a thinner construction. The weakness of the junction 34 allows the closure 32 to be separated from the funnel 28 upon application of sufficient force. The closure 32 includes a pin 36 and a plurality of projections 38, which facilitate the manual, or automated gripping of the closure 32. The projections 38 comprise a plurality of arms that extend upwardly and radially thereby forming a concave region 40 around the pin 36.

The bottom surface 24 of the well 20 includes a weakened portion 46 between the sidewall 25 and the spout portion 22. The weakened portion is formed by reducing the thickness of the thermoplastic material in the desired region. Thus, the bottom surface of the lid is made flexible in the region of the weakened portion 46 for the purpose described below.

In operation, the lid 12 is removed from the receptacle 14, a fluid sample is introduced and the lid is secured to the receptacle. For withdrawing the desired aliquot of the sample for testing purposes, the closure 32 is twisted causing the junction 34 to break and thereby exposing the opening 26. The projections 38 assist in removal of the closure 32 by providing leverage for such twisting motion. A test tube or other similar container for receiving the aliquot is inverted and placed over the spout portion 22 so that the rim of the opening of such test tube rests on the uneven bearing surface 30. Both the specimen container 10 and the test tube are then inverted thereby causing the fluid sample to fill the spout portion 22 and particularly the funnel 28. Since air is prevented from entering the container 10, the fluid sample does not leak from the opening 26. To extract the aliquot, the specimen container 10 and/or the test tube are moved towards each other causing the weakened portion 46 to flex inwardly and, in turn, forcing the spout portion 22 towards the interior of the receptacle 14. The inward movement of the spout portion 22 leads to an increase in pressure within the receptacle which, in turn, forces a portion of the fluid in the container to exit the opening and to collect in the test tube. The weakened portion 46 can be designed to deliver a specific, or controlled, volume of liquid. This is achieved by designing the weakened portion to flex by a specified amount. The specimen container is then separated from the test tube and turned upright.

In order to prevent spillage of the sample fluid after the above process, the opening 26 is closed by heat sealing. Alternatively, the closure 32 may be inverted and the pin 36 inserted into the opening 26.

The present invention serves to automate the process of utilizing a sample container as described above. More generally, the present invention provides a process for handling a container which includes:

- a cap including a precise nozzle or orifice through which the liquid sample can be ejected when a pressure differential is applied to the interior of the container;
- the cap including a flexible member which produces a pressure differential in the container when moved;
- the flexible member comprising a diaphragm covering the top of the container and having the orifice generally at the center thereof;
- a twist-off closure in the center of the cap of the container which exposes the nozzle or orifice;
- the twist-off closure being designed so as to allow it to be repeatedly and reliably manipulated by full automation.

The process of the present invention includes the following steps for handling a sample container as described above:

1. Collecting a plurality of containers in a single automation machine.
2. Selecting one container.
3. Exposing the orifice of a selected container by removing the twist-off closure by means of a series of rotary linear actuators.
4. Grasping an aliquot tube which will receive the aliquotted liquid sample.
5. Positioning the sample container and aliquot tube so that the open end of the aliquot tube is in close proximity to the exposed orifice and so that the orifice opens into the tube.
6. Inverting the sample and container and aliquot tube.
7. Applying an external force to cause the container and tube to move towards each other thereby causing flexure of the diaphragm of the container's cap. In this manner, a pressure differential is created in the container thereby causing a measured amount of the sample liquid to be ejected into the tube.
8. Separating the container and tube and reverting the container to the upright position.
9. Heat sealing the orifice of the container.
10. Transporting the tube to a sample analysis machine.

The de-capping of the sample container is provided by a mechanism whereby the sample is presented along a linear conveyor, and stopped at a termination point. The single container is isolated from other similar containers arriving along this conveyor by a series of escapements.

At the termination point, a rotary actuator closes behind the sample container, forcing it against a set of two rotating wheels; one of which is an idler, the other of which is driven by a motor. When the rotary actuator closes, and a motor is switched on, the sample container is forced to rotate.

After rotation is confirmed, an overhead linear actuator moves a gripper in place over the centre of the sample container lid, specifically above the twist-off cap. Another linear actuator then lowers a grasping fixture into a vertical position such that it surrounds the twist off cap with a 2-piece grasping fixture. A final linear actuator closes the grasping fixture onto the twist-off cap.

Upon a short time delay, determined by the mechanical properties of plastic deformation and failure of the plastic affixing the twist-off cap onto the sample container, the linear actuators then transport the twist-off cap to a disposal area. The rotating motor and the rotary actuator are disengaged from the sample container. The sample container is now de-capped.

A multi-axis transport mechanism then moves into such a position as to grasp the sample container. It does so with a grasping fixture that surrounds the sample container from two sides, in a horizontal plane such that the grasping fixture grasps the container at the point where the lid and the body of the container meet. The "fingers" of the container surround the container and offer a mechanical surface upon which force can be applied coaxially with the centreline of the sample container, in a direction from the bottom of the container towards the cap of the container, such that the grasping location of the fixture relative to the container remains unchanged during and after the exertion of such force. The grasping fixture also contains a compliance mechanism aligned in the direction of this controlled external force such that the external force is isolated to the sample container and the grasping fixture, but does not impose any such loading upon the transport mechanism which moves the grasping fixture.

The grasping fixture for the sample container is coaxially aligned with another grasping fixture designed to grasp the aliquot tubes. This secondary grasping fixture also contains a compliance device which works coaxially with the compliance device for the grasping fixture for the sample container. In so doing, it permits the application of a load coaxially with the centreline of the aliquot tube. It also isolates the transport mechanism from this external load. Together, the grasping fixtures (complete with their compliance devices) comprise the "end effector" of the transport mechanism.

The transport mechanism offers translational and rotational degrees of freedom such that the sample container and aliquot tubes acquired from different locations and brought together in an orientation so that the sample container is located at a higher position than the aliquot tube, and so that the action of exerting an external force relative to the closed end of the aliquot tube and the grasping fixture for the sample containers will displace the two containers relative to each other and will exercise the diaphragm in the lid of the sample container, causing the displacement of a portion the liquid sample into the aliquot tube.

The transport mechanism offers translational and rotational degrees of freedom such that the aliquot tube and sample containers can be re-positioned after this process is performed so that they can be handled by other equipment.

Figure 2:
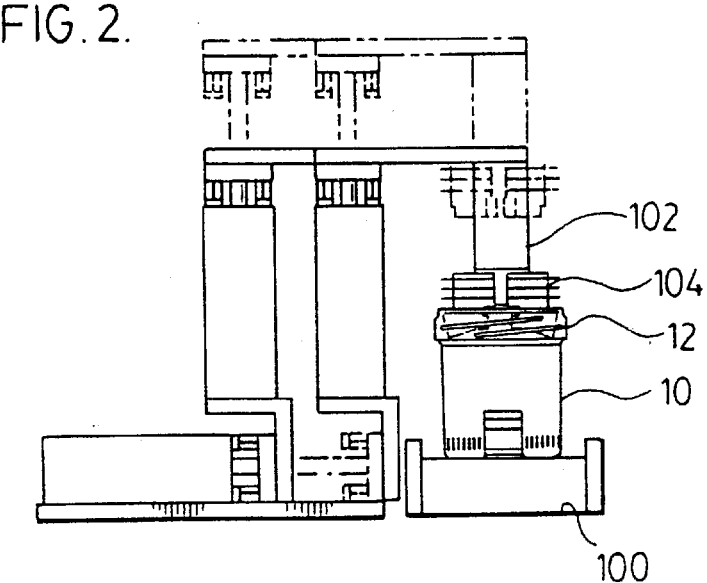
FIG. 2 is a side elevation of an apparatus for opening the sample container.

FIG. 2 illustrates one portion of the apparatus of the invention wherein the twist off closure of the lid 12 of the container 10 is removed to expose the orifice. The container is first positioned on a stage 100. Subsequently, a grasping arm 102 to which is attached a rotating gripping means 104 is lowered towards the lid 12. The gripping means 104 engages the twist off closure 32 and rotates the closure thereby breaking the junction 34 to separate the closure 32 from the rest of the lid and exposing the opening 26.

Figure 3:
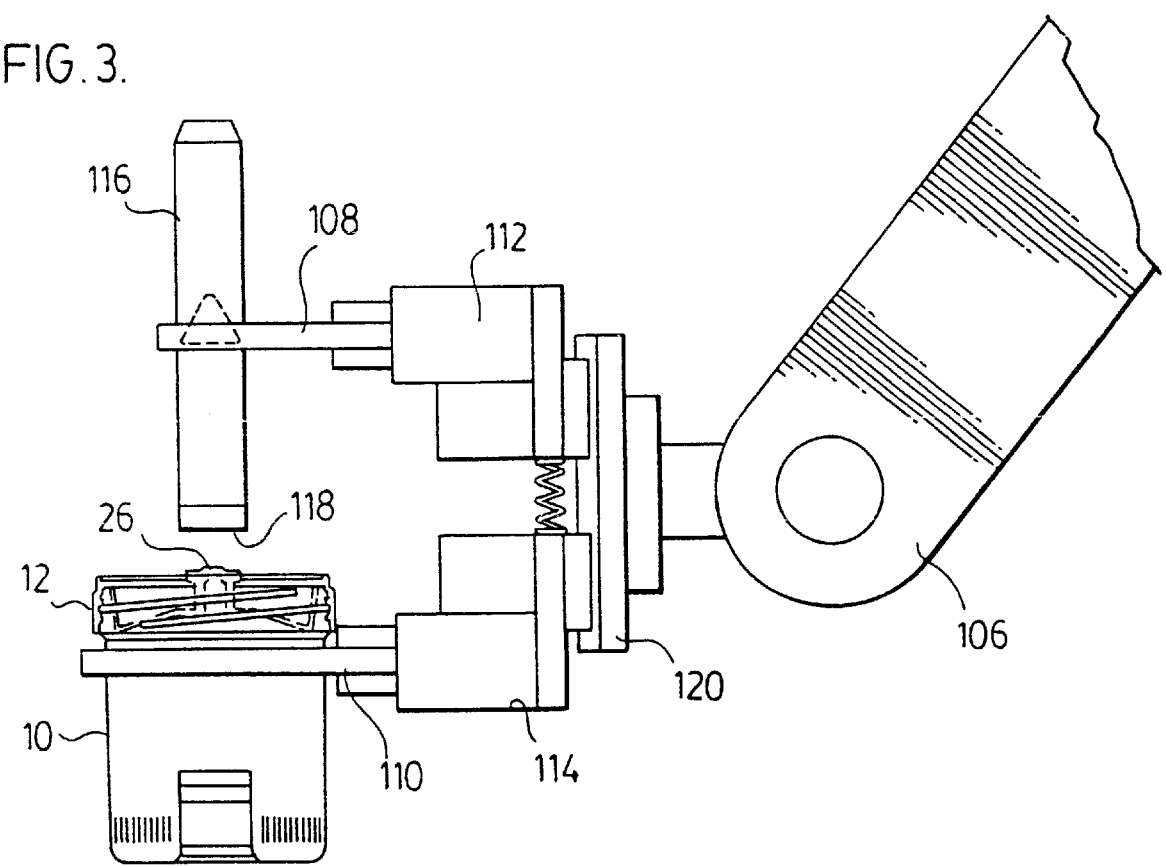
FIG. 3 is a side elevation of an apparatus for positioning the sample container and aliquot tube prior to transferring the aliquot.

As shown in FIG. 3, first and second grasping fingers 108 and 110 are attached to actuators 112 and 114 respectively. Fingers 108 and 110 are used to grasp an aliquot tube 116 and the sample container 10 from which the closure has been removed. The fingers 108 and 110 maintain tube 116 and container 10 in an opposing arrangement wherein the opening 118 of the tube 116 is positioned opposite the orifice 26. The actuators 112 and 114 are joined to a plate 120 which is rotatably attached to arm 106.

Figure 4:
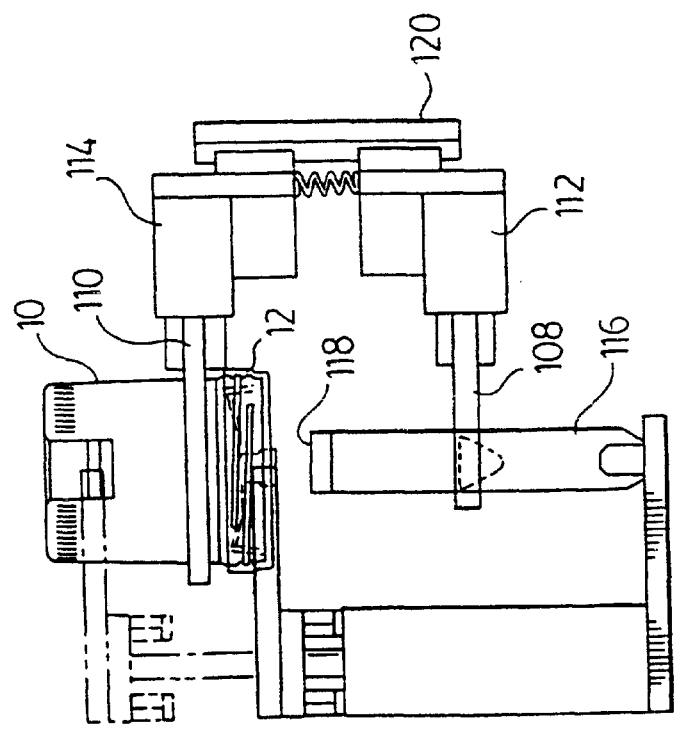
FIG. 4 is a side elevation of an apparatus for causing the transfer of a sample aliquot.

As shown in FIG. 4, the plate 120 is rotated 180° so as to invert both the container 10 and the aliquot tube 116. The actuators 112 and 114 are then urged towards each other so as to press the tube 116 against the lid 12 of container 10 and thereby eject an aliquot of the sample liquid into the tube 116 as mentioned above.

Figure 5:
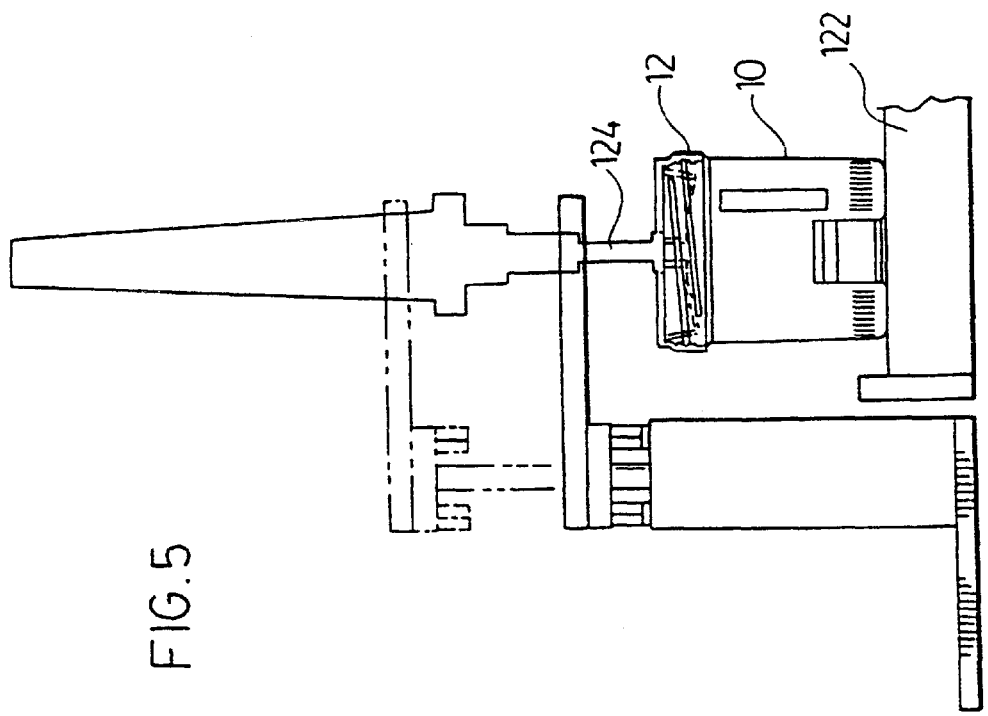
FIG. 5 is a side elevation of an apparatus for sealing the container after transferring the aliquot.

Following delivery of the desired aliquot, the container 10 is then reverted to the upright position and transferred to a sealing station as illustrated in FIG. 5. As shown, the container 10 is placed on a stage 122 and a heating iron 124 is lowered onto the orifice on the lid 12. Heating iron 124 melts the thermoplastic material from which the lid is formed and thereby seals the orifice.

The tube 116 is then transported to an analyzer for the appropriate testing on the sample aliquot.

Figure 6:
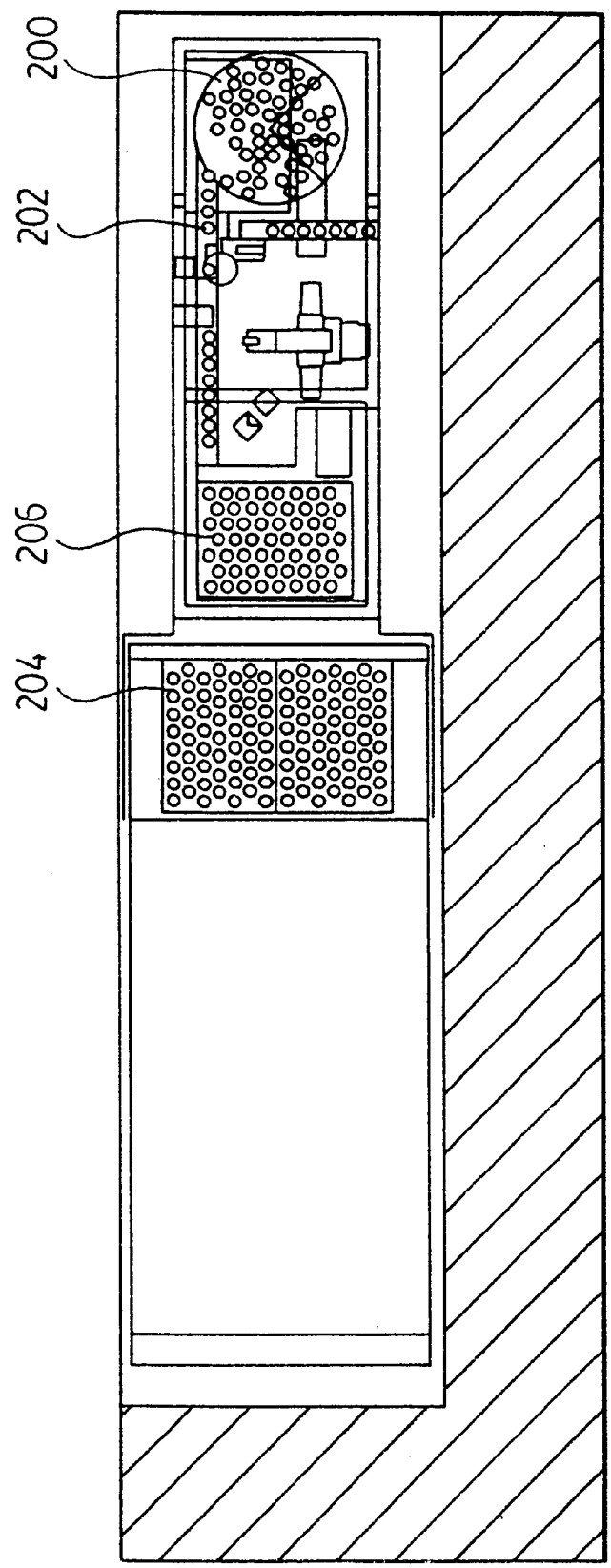
FIG. 6 is a plan view of a complete apparatus for the process of the invention.

FIG. 6 illustrates a plan view of a suggested arrangement of the apparatus of the invention wherein the containers to be processed are located in a collection area 200. Collection area 200 preferably comprises a rotating turntable which diverts the containers to the outer circumference to form a single row of containers 202. The single row of containers is then fed to the various stations described above. After the completing the above steps, the sealed container is placed in a storage unit 204. However, in the event that the test on the sample is positive, the container from which the sample was taken is placed in a positives area 206.

Figure 7:
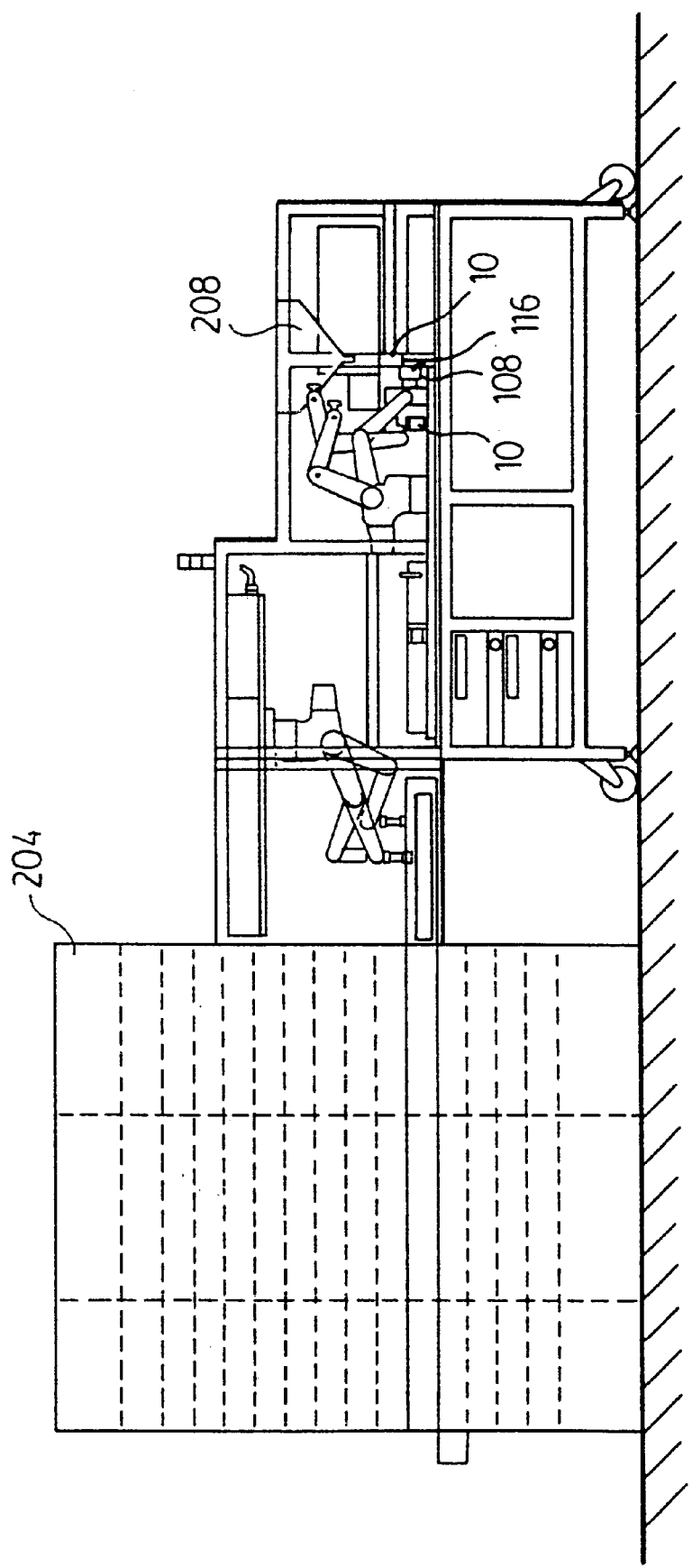
FIG. 7 is a side elevation of a complete apparatus for the process of the invention.

FIG. 7 illustrates a further view of the complete apparatus which also shows the aliquot tube feeder 208.

In the preferred embodiment, a labeling station is provided wherein the container and aliquot tube are labeled with a bar code so as at identify each pair.

Although the invention has been described with reference to certain specific embodiments, various modifications thereof will be apparent to those skilled in the art without departing from the spirit and scope of the invention as outlined in the claims appended hereto.

What is claimed is:

1. An apparatus for extracting a liquid sample from a sample container into an aliquot tube, the container having a lid including a flexible flange for covering an opening of said container, the lid further including an opening sealed by a twist-off closure, the apparatus comprising:

a) a means for grasping said container;

b) a first robotic arm having a rotating grip, said grip being adapted for gripping and disengaging said twist-off closure, and thereby un-sealing said container;

c) a second robotic arm having a first grasping means for grasping said un-sealed container and a second grasping means for grasping an aliquot tube, said second robotic arm being adapted to maintain said aliquot tube in an inverted position above the opening of said container;

d) said second robotic arm further being rotatable whereby said aliquot tube and said container may be rotated simultaneously to invert said container and right said aliquot tube;

e) said first and second grasping means on said second robotic arm being adapted to be moved towards each other for biasing said aliquot tube and/or said container against each other whereby said flexible flange of said lid is forced to bend and, thereby, expel a volume of said liquid into said aliquot tube;

f) a means for separating said container and said aliquot tube;

g) a means for sealing the opening on said container lid; and, h) a means for conveying said aliquot tube to a location for conducting any required tests on the extracted sample.

* * * * *